(12) United States Patent
Scheibe et al.

(10) Patent No.: US 8,308,659 B2
(45) Date of Patent: Nov. 13, 2012

(54) BI-DIRECTIONAL SHEATH DEFLECTION MECHANISM

(75) Inventors: Grant A. Scheibe, Loretto, MN (US); Mark Nelson, Plymouth, MN (US)

(73) Assignee: Greatbatch Ltd., Clarence, NY (US)

( * ) Notice: Subject to any disclaimer, the term of this patent is extended or adjusted under 35 U.S.C. 154(b) by 471 days.

(21) Appl. No.: 12/463,570

(22) Filed: May 11, 2009

(65) Prior Publication Data

US 2009/0281524 A1   Nov. 12, 2009

Related U.S. Application Data

(60) Provisional application No. 61/051,959, filed on May 9, 2008.

(51) Int. Cl.
| | |
|---|---|
| *A61B 5/00* | (2006.01) |
| *A61M 25/00* | (2006.01) |
| *A61M 31/00* | (2006.01) |
| *A61M 37/00* | (2006.01) |

(52) U.S. Cl. ............ 600/585; 604/95.04; 604/523; 604/528

(58) Field of Classification Search ........... 600/146, 600/434, 435, 585; 604/95.04, 93.01, 506–508, 604/523, 528

See application file for complete search history.

(56) References Cited

U.S. PATENT DOCUMENTS

| | | | |
|---|---|---|---|
| 4,294,233 A | | 10/1981 | Takahashi |
| 5,944,690 A | | 8/1999 | Falwell et al. |
| 6,059,739 A | * | 5/2000 | Baumann ............... 600/585 |
| 7,524,301 B2 | | 4/2009 | Dubois et al. |
| 7,691,095 B2 | | 4/2010 | Bednarek et al. |
| 2006/0184106 A1 | * | 8/2006 | McDaniel et al. ......... 604/95.04 |
| 2007/0260223 A1 | * | 11/2007 | Scheibe et al. ............... 604/528 |
| 2010/0004592 A1 | | 1/2010 | Butler |
| 2010/0069834 A1 | | 3/2010 | Schultz |
| 2010/0164137 A1 | | 7/2010 | Selkee |

FOREIGN PATENT DOCUMENTS

| | | |
|---|---|---|
| EP | 1323448 A2 | 7/2003 |
| WO | 9505116 | 2/1996 |
| WO | 9637252 | 11/1996 |

OTHER PUBLICATIONS

European Search Report. Application No. 09159950.6-2320. Sep. 15, 2009.

* cited by examiner

*Primary Examiner* — Jeffrey G Hoekstra
*Assistant Examiner* — Megan Leedy
(74) *Attorney, Agent, or Firm* — Michael F. Scalise

(57) ABSTRACT

A deflectable sheath for use in medical procedures in the vasculature is described. The sheath includes a handle supporting the sheath. Two pull wires run along opposite sides of the sheath to anchors at the deflectable distal end. The handle includes a rotatable member that moves a threaded member including wire guide in a back and forth translation. As the movement occurs, force is applied to either one or the other of the pull wires to cause deflection of distal end of the sheath in either and upwardly or a downwardly direction with respect to the longitudinal axis of the sheath.

32 Claims, 12 Drawing Sheets

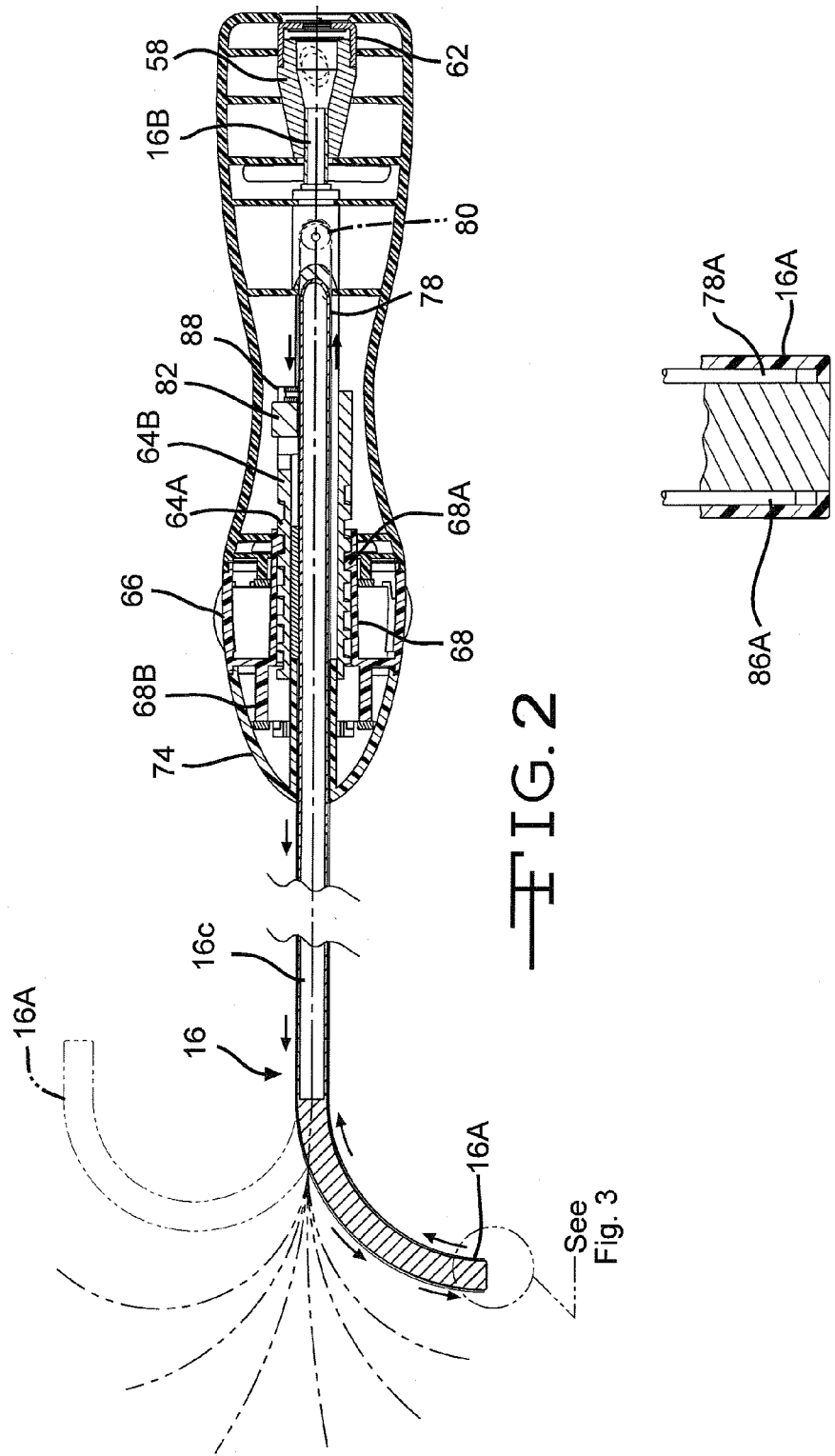

BI-DIRECTIONAL SHEATH DEFLECTION MECHANISM

CROSS-REFERENCE TO RELATED APPLICATION

This application claims priority from U.S. provisional Application Ser. No. 61/051,959, filed May 9, 2008.

BACKGROUND OF THE INVENTION

Field of the Invention

The present invention generally relates to medical devices such as deflectable sheaths. More particularly, the present invention relates to a steering system for positioning the deflectable distal end of a sheath in a desired orientation.

SUMMARY OF THE INVENTION

Many current deflectable sheaths include a pull wire that extends from the distal end of the sheath to a deflection control actuator located in a handle. The pull wire may only be tensioned in one direction thereby providing for deflection in a single direction. Compression of the pull wire in another direction can buckle the wire. This substantially prevents active deflection of the sheath with the deflection control actuator in more than one direction. Straightening of the sheath in a direction opposed to that granted by tensioning the pull wire is thereby accomplished with the natural elasticity of the sheath distal end. The deflected sheath exerts a passive pulling force on the pull wire that straightens the sheath without active control through the deflection control actuator. Further, the elasticity of the sheath only straightens the distal end without providing for deflection of the sheath in an opposed direction.

What is needed is a deflectable sheath that overcomes the shortcomings of previous designs by providing for active deflection of the distal end in more than one direction or orientation.

SUMMARY OF THE INVENTION

The present invention relates to a novel design for a deflectable sheath for use in medical procedures, particularly where access to the vasculature is needed. The deflectable sheath comprises a tubular sheath providing a delivery lumen extending from a proximal portion to a deflectable distal sheath end. A handle is supported on the proximal sheath portion. First and second pull wires extend from the handle along the sheath to the deflectable distal sheath end. They are captured in a slidable relationship between the sheath and a liner except at the deflectable distal end of the sheath to which they are anchored. A threaded member is housed in the handle and comprises a cylindrical bore that receives the proximal sheath portion in a longitudinally slidable relationship. The threaded member includes a carriage carrying a wire guide retainer. That way, when a rotatable member of the handle is rotated, it causes the threaded member to translate in either a forwardly or backwardly direction along the proximal portion of the sheath.

A first pull wire extends from a first distal end anchored to the deflectable distal sheath end, past the wire guide retainer to a proximal pulley and then back through a first bore in the wire guide retainer to a proximal first pull wire end provided with a first stop member located distally of the wire guide retainer. A second pull wire extends from a second distal end at the deflectable distal sheath end and through a second bore in the wire guide retainer to a proximal second pull wire end provided with a second stop member located proximally of the wire guide retainer.

Then, when the rotatable member is manipulated in a first direction, the threaded member and the carriage carrying the wire guide retainer translate along the proximal sheath portion in a forwardly direction against the first stop member to apply a first pulling force on the first pull wire. This force causes the distal sheath end to deflect into a first orientation out of alignment with respect to a longitudinal axis of the sheath. On the other hand, when the rotatable member is manipulated in a second direction, opposite the first direction, the threaded member carrying the wire guide retainer translates along the proximal sheath portion in a rearwardly direction against the second stop member to apply a second pulling force on the second pull wire. This force causes the distal sheath end to deflect into a second orientation out of alignment with respect to the longitudinal axis of the sheath. The second deflection direction is generally opposite that of the first deflection direction.

The foregoing and additional advances and characterizing features of the present invention will become clearly apparent upon reading the ensuing description together with the included drawings wherein:

BRIEF DESCRIPTION OF THE DRAWINGS

FIG. 2 is a cross-sectional view along line 2-2 of FIG. 1 showing the deflectable distal end 16A of the sheath 16 deflected in opposite directions.

FIG. 3 is an enlarged view of the indicated area in FIG. 2.

DETAILED DESCRIPTION OF THE PREFERRED EMBODIMENTS

Figure 1:
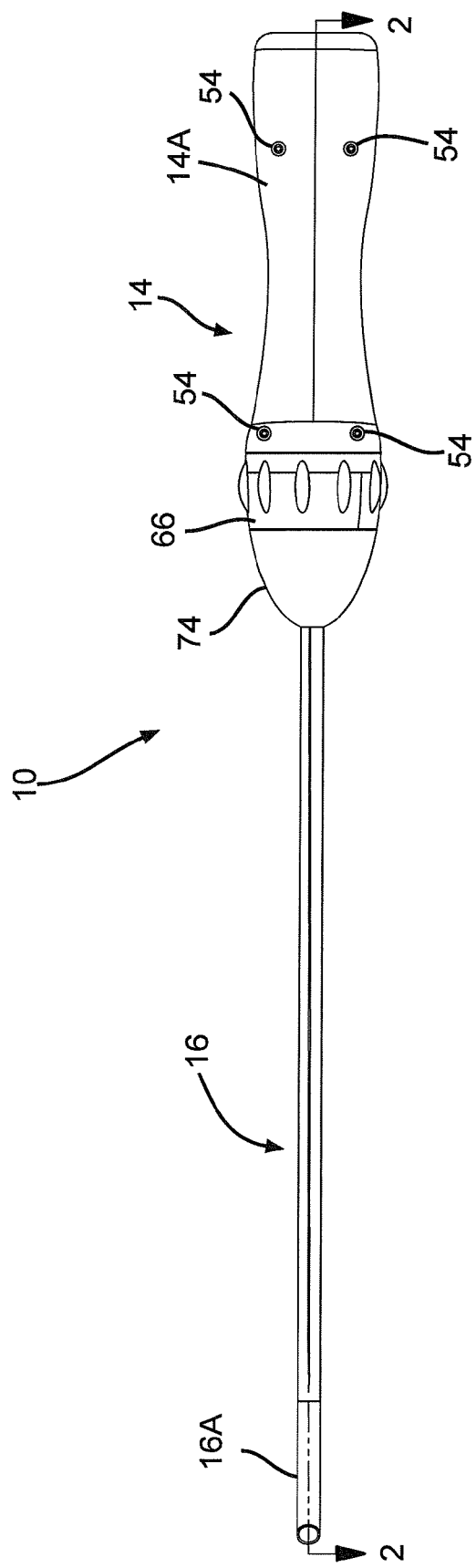
FIG. 1 is a perspective view of a bi-directional sheath assembly 10 according to the present invention.

Turning now to the drawings, FIG. 1 illustrates a bi-directional sheath assembly 10 according to the present invention.

The bi-directional sheath assembly 10 comprises a handle assembly 14 supporting a deflectable sheath 16.

The deflectable sheath 16 comprises an elongate tubular structure that is flexible yet substantially non-compressible along its length. The deflectable sheath 16 extends from a deflectable distal end 16A (FIG. 2), which is adapted to be disposed within a patient, to a proximal portion 16B. The sheath 16 includes a delivery lumen 16C that extends through the sheath body from the deflectable distal end 16A to the proximal portion 16B. An exemplary construction comprises the sheath 16 as a tubular member formed of a polymeric material, such as of PEBAX, encasing a tubular wire braided as a mesh. A liner of a second polymeric material, for example PTFE, resides inside the PEBAX tube. The PTFE liner provides the sheath lumen 16C with sufficient lubricity so that medical instruments, devices, and the like, slide through the sheath 16 with a minimal amount of force. The delivery lumen 16C is sized and shaped to receive, for example, instruments, fluids, media, and the like. The handle assembly 14, in turn, provides for selective deflection of a distal end 16A of the sheath 16 into anyone of a number of disparate orientations, as will be further described in detail herein below.

Figure 4:
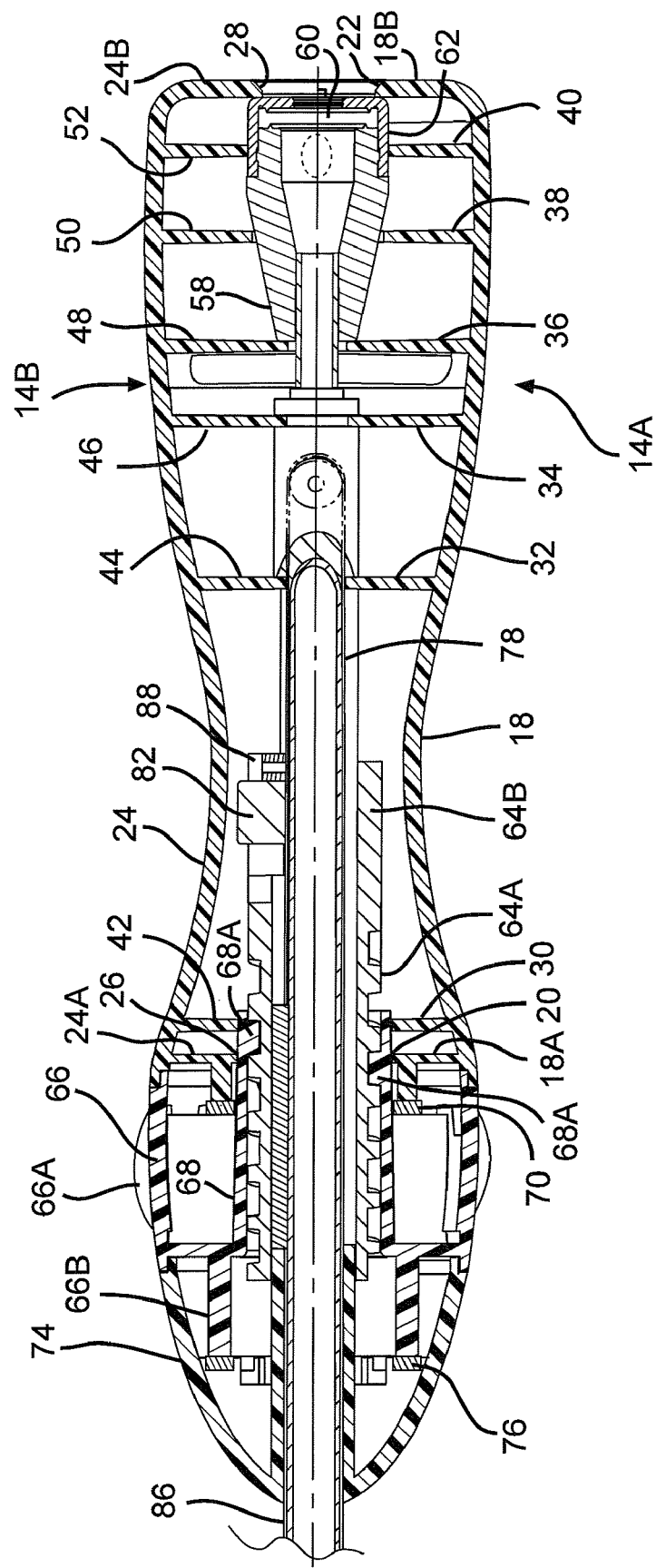
FIG. 4 is a cross-sectional view of the handle assembly 14 of the bi-directional sheath 10 shown in FIG. 1.
Figure 5:
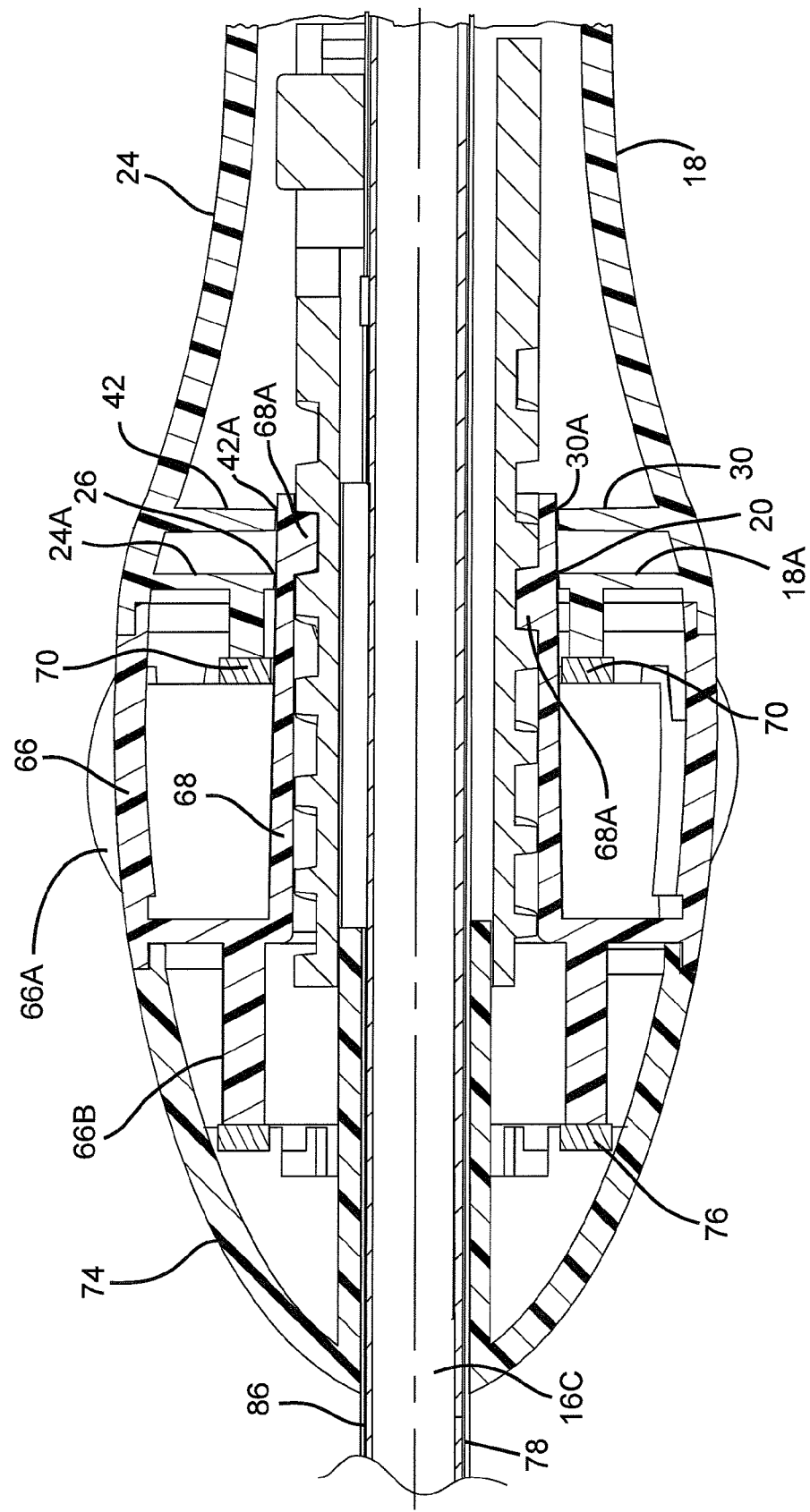
FIG. 5 is an enlarged cross-sectional view of a distal portion of the handle assembly 14 shown in FIG. 4.

As shown in FIGS. 2 and 4 to 14, the handle assembly 14 includes a lower handle portion 14A and an upper handle portion 14B. The lower handle portion 14A comprises a lower sidewall 18 having an ergonomically designed curved shape, the extent of which is defined by a distal end wall 18A and a proximal end wall 18B, both meeting spaced apart front and back edges 18C and 18D. The distal end wall 18A includes a semi-circular opening 20 (FIG. 5). Likewise, the proximal end wall 18B has a semi-circular opening 22 (FIGS. 4 and 5) therein.

Similarly, the upper handle portion 14B comprises an upper sidewall 24 having an ergonomically designed curved shape defined by a distal end wall 24A having a semi-circular opening 26 (FIG. 4) and a proximal end wall 24B provided with a semi-circular opening 28 (FIGS. 4 and 5), both meeting spaced apart front and back edges 24C and 24D.

Figure 6:
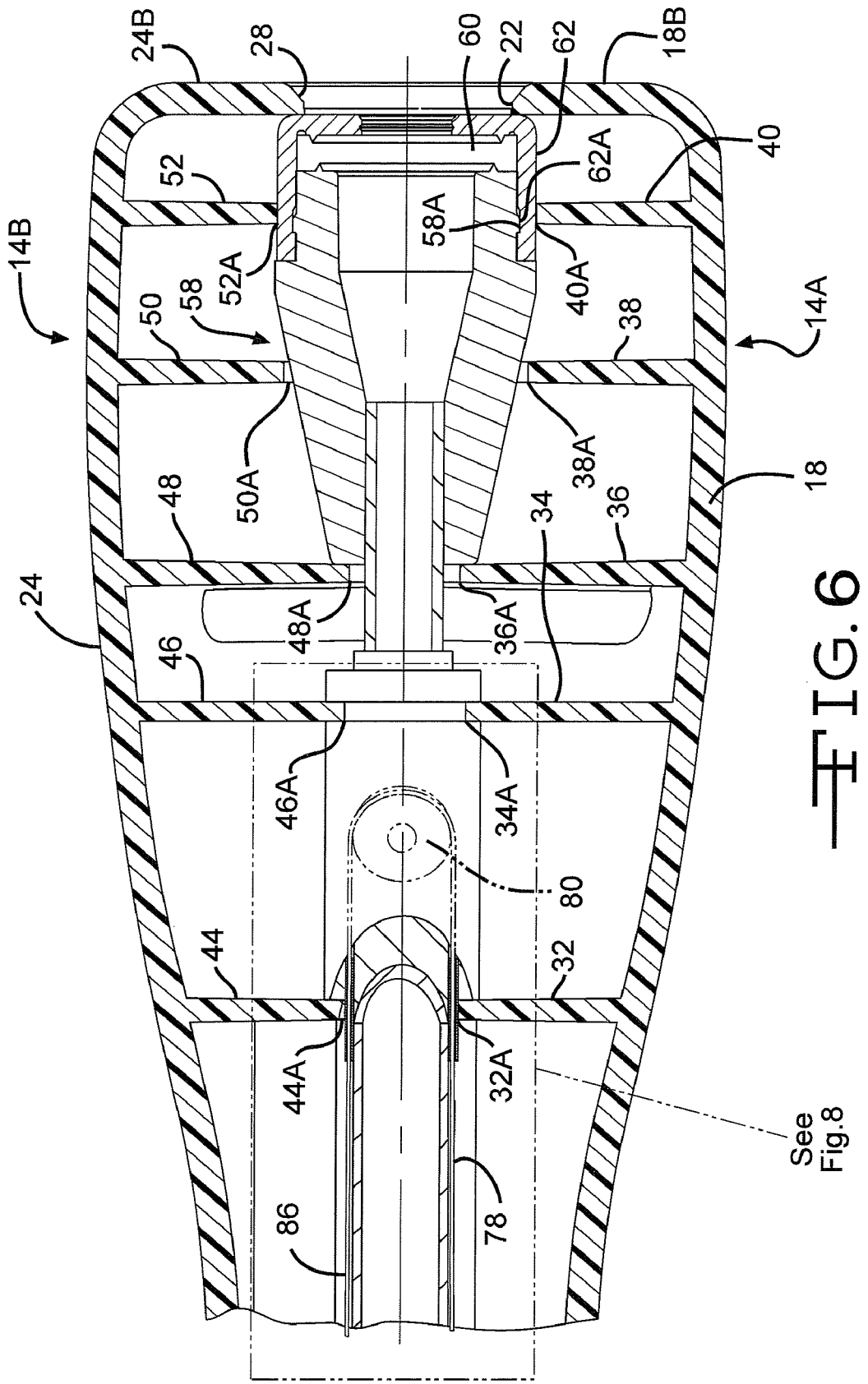
FIG. 6 is an enlarged cross-sectional view of a proximal portion of the handle assembly 14 shown in FIG. 4.

As shown in FIGS. 4 to 6, the lower handle portion 14A further includes a plurality of interior ribs spaced along its length. In an orientation looking from the distal end wall 18A toward the proximal end wall 18B, these ribs comprise a first interior rib 30, a second interior rib 32, a third interior rib 34, a forth interior rib 36, a fifth interior rib 38 and a sixth interior rib 40. The first interior rib 30 is closest to the distal end wall 18A while the sixth interior end wall is closest to the proximal end wall 18B. The ribs 30, 32, 34, 36, 38 and 40 have respective openings 30A, 32A, 34A, 36A, 38A and 40A therein; however, the openings are not of an identical shape.

As shown in FIGS. 4 to 6, the upper handle portion 14B comprises a corresponding number of interior ribs 42, 44, 46, 48, 50 and 52 provided with respective openings 42A, 44A, 46A, 48A, 50A and 52A as those shown and described with respect to the lower handle portion 14A. That way, when the handle portions 14A, 14B are mated to each other, the spaced apart longitudinal edges 24C and 24D of the upper handle portion 14B snap fit into a mated relationship with the edges 18C, 18D of the lower handle portion 14A. As shown in FIG. 1, screws 54 received in openings 56 in the lower handle portion 14A thread into receptacles in the upper handle portion 14B to secure the handle portion together.

FIG. 6 is an enlarged view showing a hub 58 over-molded onto the proximal sheath portion 16B. The hub 58 has a tapered shape that serves to funnel and direct instruments and the like into the sheath lumen 16C. The proximal portion of the hub 58 has a generally cylindrical shape. A sealable membrane 60 is seated against the proximal hub portion, captured there by a cap 62. The cap 62 includes an annular groove 62A that snap-fits into engagement with an annular protrusion 58A on the outer wall of the hub 58.

Figure 7:
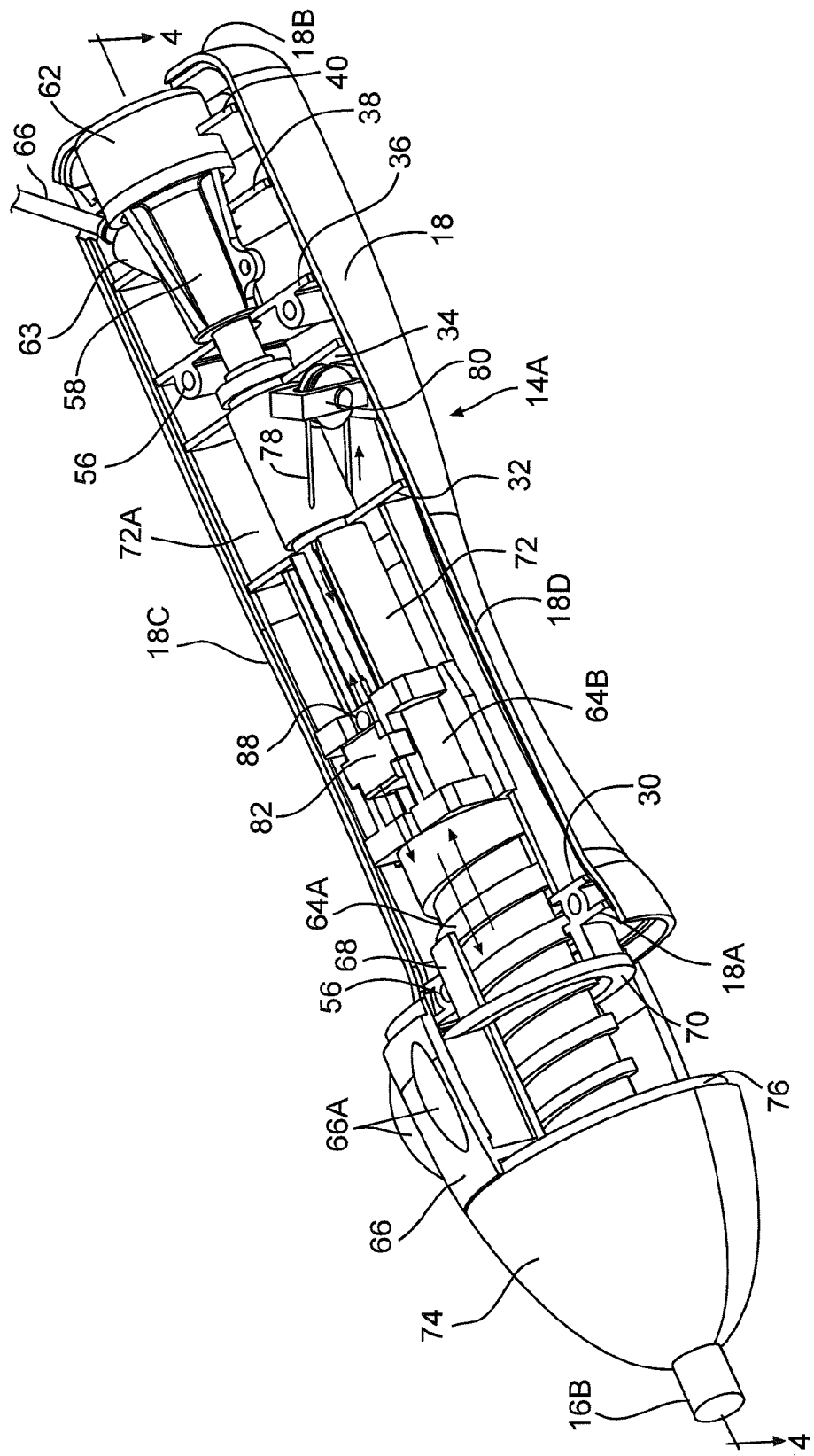
FIG. 7 is a broken away perspective view of the handle assembly 14.
Figure 8:
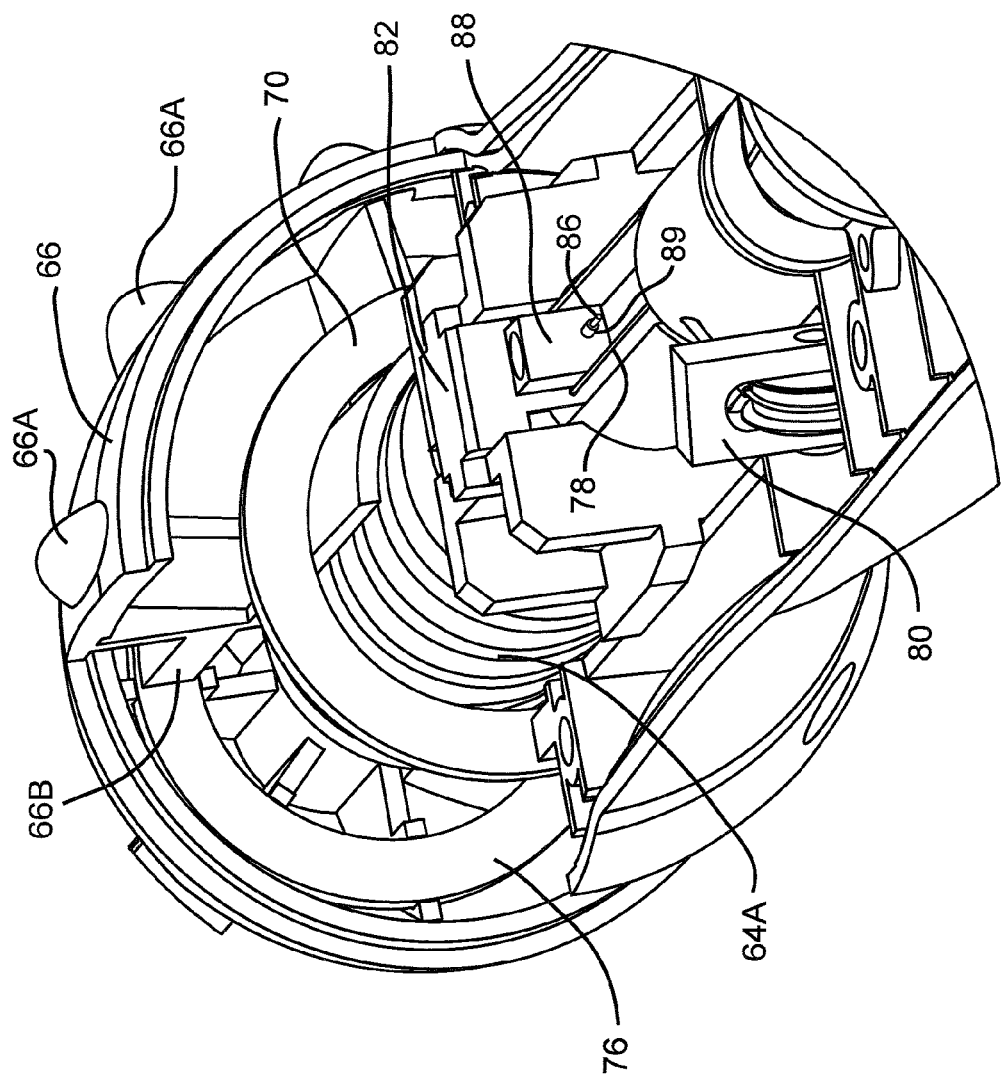
FIG. 8 is a perspective view of the distal end of the handle assembly 14.
Figure 9:
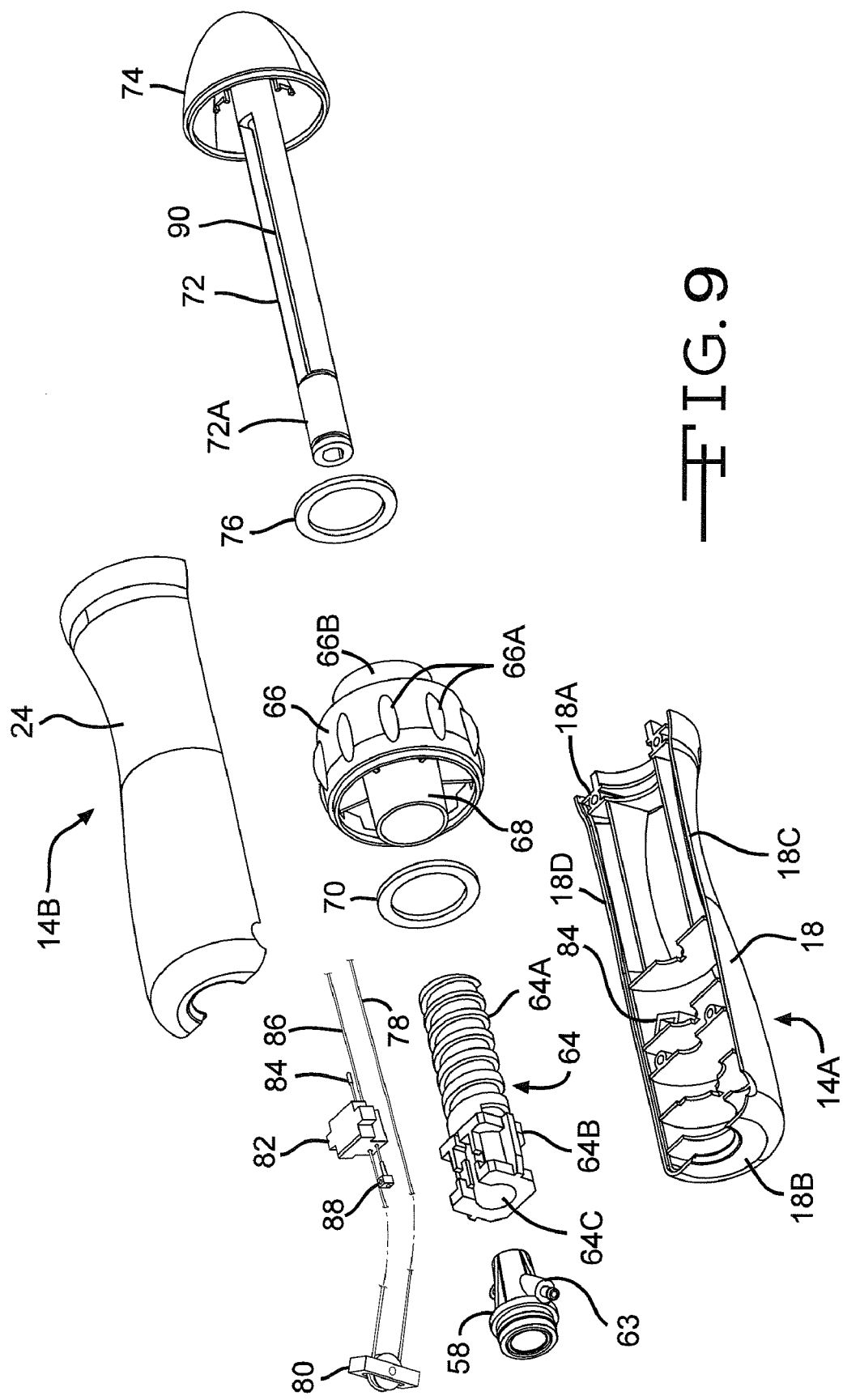
FIG. 9 is an exploded view of the main components of the handle assembly 14.

As shown in FIG. 7, a side port 63 exits through the wall of the hub 58 with its end terminating short of the lower sidewall 18. The side port 63 allows for the introduction of fluids such as saline or medicine through the sheath 16 without having to remove instruments disposed through the sheath lumen 16C. A flexible tube 66 connected to the port 63 exits the lower and upper sidewalls 18, 24 and facilitates the introduction of fluids therein.

As shown in FIGS. 2, 4, 5, 7 and 10 to 12, a lead screw assembly 64 comprises a distal threaded portion 64A and a proximal carriage portion 64B. A lumen 64C of a relatively large diameter extends the entire length of the lead screw assembly 64.

A rotatable knob 66 includes a sleeve 68. The rotatable knob 66 and sleeve 68 are a unitary molded member provided with a plurality of oval-shaped protrusions 66A spaced radially about the periphery thereof. The protrusions 66A serve as gripping surfaces to provide a physician using the present bi-directional sheath 10 with better tactile feel.

Figure 10:
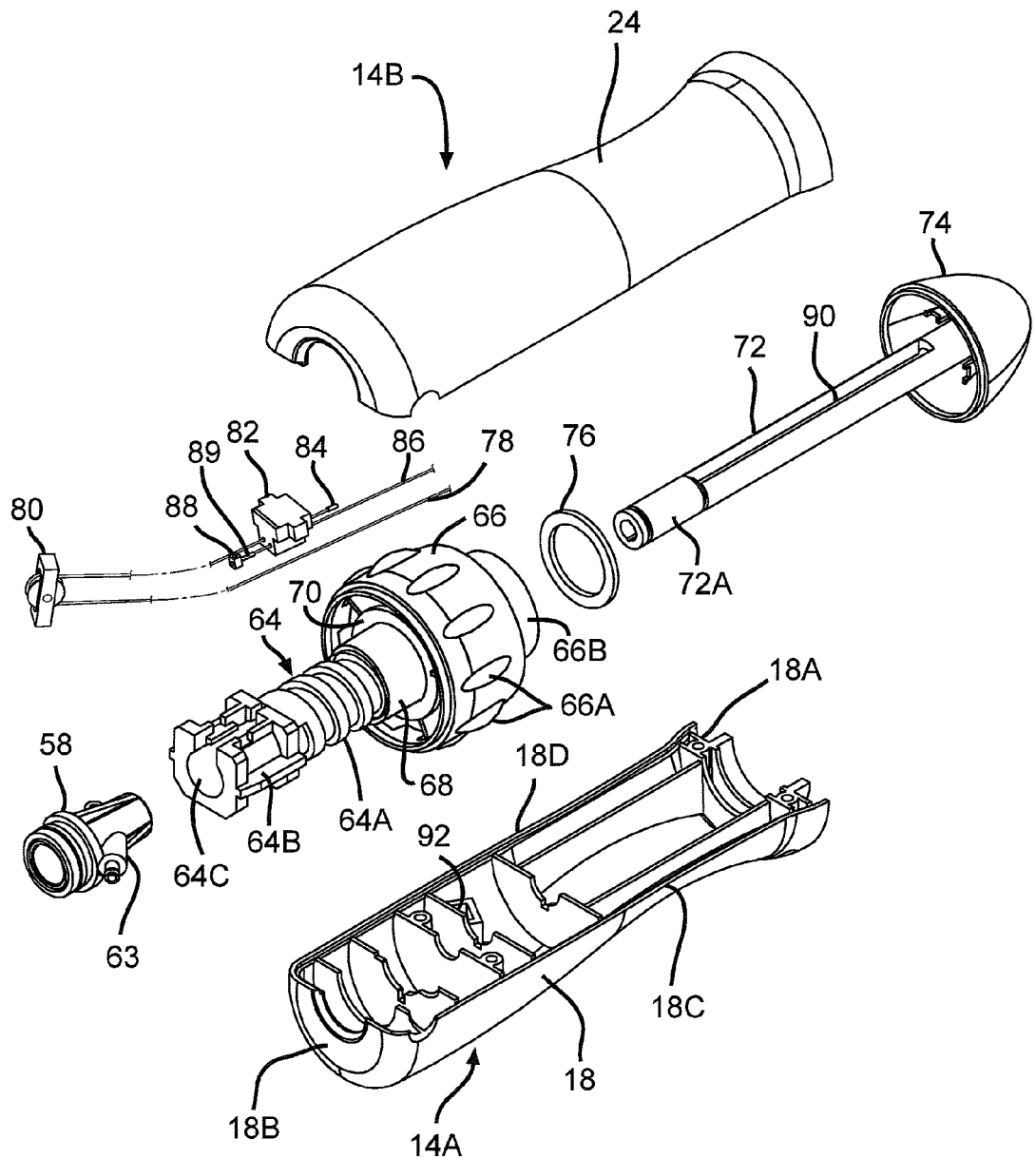
FIG. 10 is an exploded view showing some of the handle components of the FIG. 9 after having been partially assembled.

During the assembly process, a first friction washer 70 is moved onto the sleeve 68 until it abuts the rotatable knob 66. The sleeve 68 carrying the rotatable knob 66 is then threaded onto the threaded portion 64A (FIG. 10). The sleeve 70 can be provided with one or more internal threads 68A (FIGS. 4 and 5) or a post that match the threads of the lead screw assembly 64. For a more detailed description of such a construction for a rotatable actuator including a sleeve that threads into engagement with a screw, reference is made to U.S. Patent Application Pub. No. 2007/0260223 to Scheibe et al. This application is assigned to the assignee of the present invention and incorporated herein by reference.

Figure 11:
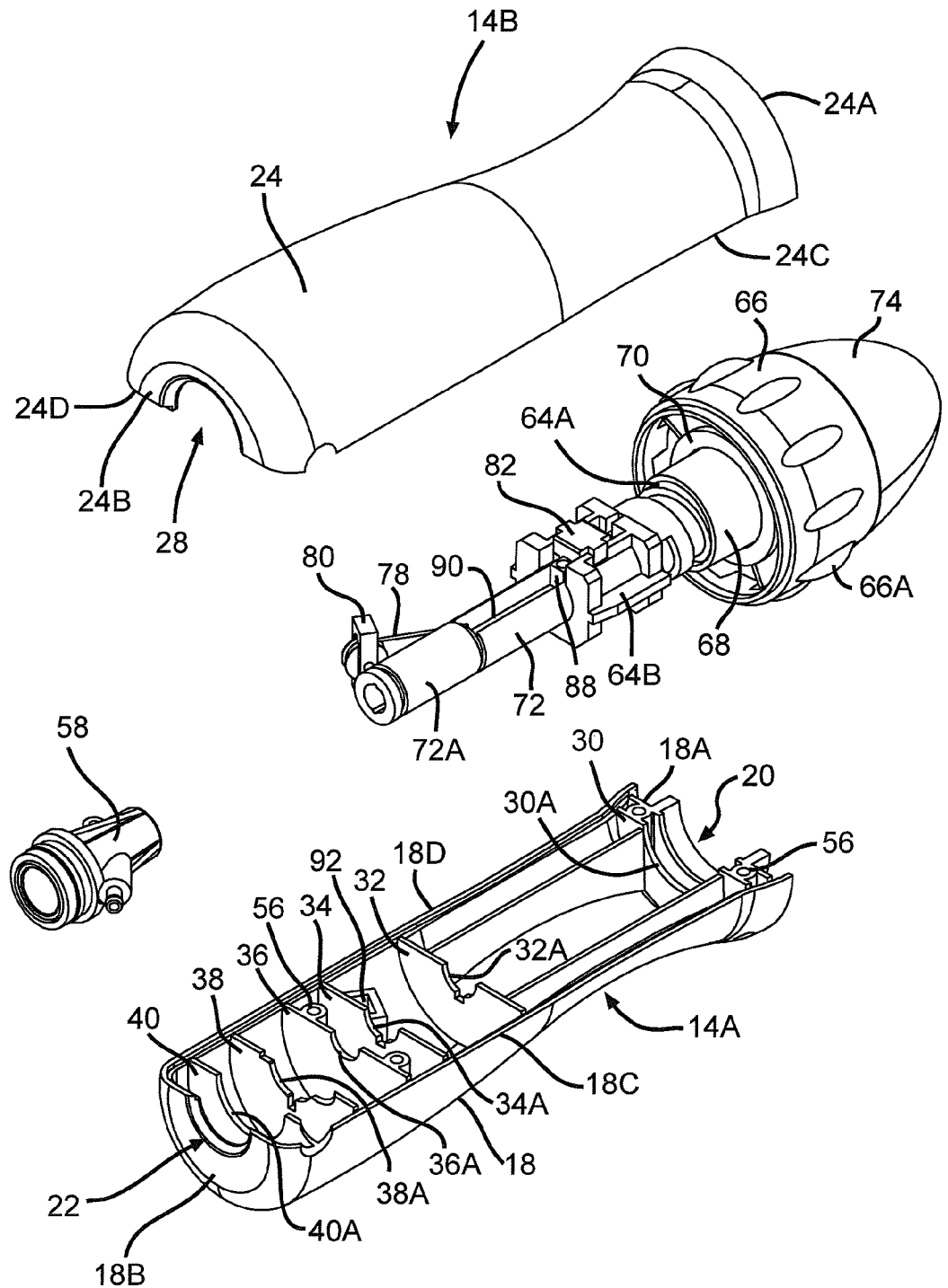
FIG. 11 is an exploded view showing further assembly of the handle components of the FIG. 10.
Figure 12:
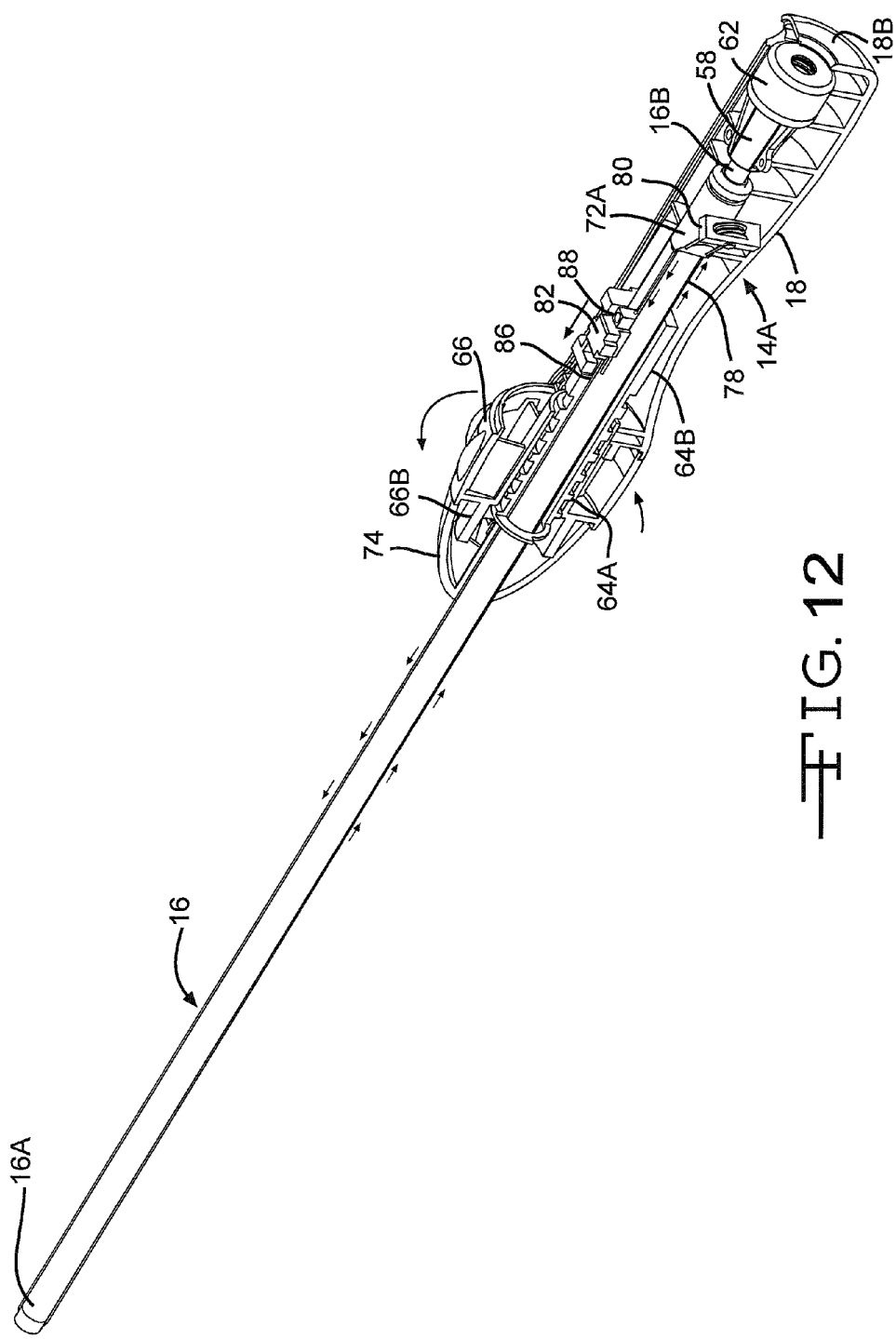
FIG. 12 is a pertly broken away perspective view of the assembled handle 14 and the sheath 16.

A hollow support shaft 72 has a tapered nose cone 74 supported at a distal end thereof. The support shaft 72 is received through the threaded portion 64A of the lead screw 64 having the rotatable knob 66 and sleeve 68 threaded thereon. This continues until a distal sleeve portion 66B of the rotatable knob 66 is fitted inside the nose cone 74 (FIG. 11). A second friction washer 76 is captured between the distal end of the sleeve portion 66B and an interior surface of the nose cone 74.

The support shaft 72 including the nose cone 74, the rotatable knob 66 and sleeve 68 threaded onto the threaded portion 64A of the lead screw 64 and the friction washers 70, 76 as a subassembly is now slid over the distal end 16A of the sheath 16 and moved along the length thereof until it abuts the tapered end of the hub 58 over-molded onto the proximal sheath portion 16B. The support shaft 72 has an inner diameter that fits snuggly over the sheath 16 and an outer diameter that is snuggly received inside the lumen 64C of the lead screw 64 while the sleeve 68 of the rotatable actuator 66 is threadingly received over the threaded screw portion 64A. In that position, the proximal portion 16B of the sheath 16 extends through the support shaft 72 including the nose cone 74.

A first pull wire 78 is provided. The first pull wire 78 can be made of such disparate material as stainless steel, NITINOL®, or flexible polymers and textile materials such as VECTRAN® or Spectra. The first pull wire 78 extends from the deflectable distal end 16A of the sheath, along and through the sheath body 16 and a pulley 80 to a wire guide retainer 82 before terminating at a first hypo-tube 84 serving as a first stop member. The pulley 80 serves to change the direction and point of application of a pulling force applied to the first pull wire 78, as will be described in detail herein after.

The pulley 80 is exemplary of a device for this function. In that respect, the first pull wire 78 could be partially wrapped around a spool/wheel mechanism or a post serving as structures for changing the direction and point of application of a pulling force applied thereto.

The first hypo-tube 84 is clamped, swaged or otherwise secured to the end of the first pull wire 78 and resides on the distal side of the wire guide retainer 82 with respect to the proximal end of the handle assembly 14. While the first pull wire 78 is fixedly secured to the first hypo-tube 84, it is in a slidable relationship with the wire guide retainer 82.

While not shown in the drawings, an anchor couples between the distal end 78A of the first pull wire 78 (FIG. 3) and the sheath body 16 at the deflectable distal end 16A. For a more thorough understanding of an anchor for the deflectable distal tip of a sheath, reference is made to U.S. Pat. No. 7,497,853 to Fischer et al. This patent is assigned to the assignee of the present invention and incorporated herein by reference.

A second pull wire 86, preferably made from similar material as the first pull wire 78, extends from the deflectable distal end 16A of the sheath, along and through the sheath body 16, through the guide wire retainer 82 before terminating at a wire clamp block 88 secured to a second hypo-tube 89 at the proximal end of the wire 86. The wire clamp block 88 is preferably secured to the second hypo-tube 89 at the proximal end of the second pull wire 86 by a set screw received in the block and serves as a second stop member. In an alternate embodiment, the wire clamp block 88 and the second hypo-tube 89 can be combined as a unitary second stop member.

The wire clamp block 88 resides on the proximal side of the wire guide retainer 82 with respect to the hypo-tube 84 secured to the end of the first pull wire 78. The second hypo-tube 89 and, consequently, the second pull wire 86 are in a slidable relationship with the wire guide retainer 82. While not shown in the drawings, an anchor couples between the distal end 86A of the second pull wire 86 (FIG. 3) and the sheath body 16 at the deflectable distal end 16A.

In that respect, both the first hypo-tube 84 secured to the end of the first pull wire 78 and the wire clamp block 88 secured to the second hypo-tube 89 at the proximal end of the second pull wire 86 serve as stops for their respective pull wires. As will be described in detail hereinafter, pulling forces imparted to the wires 78, 86 by manipulation of the rotatable knob 66 of the handle assembly 14 are transmitted by one or the other of the pull wires 78, 86 to the deflectable distal end 16A of the sheath 16 to cause deflection thereof in an intended manner.

After the support shaft 72 is moved along the length of the sheath 16 until it abuts the hub 58, the first and second pull wires 78, 86 are nested in diametrically opposed longitudinal grooves 90 (only one shown in FIGS. 9 and 10) in the support shaft 72.

The hub 58, the lead screw assembly 64, the rotatable knob 66 threaded thereon, the support shaft 72 including the nose cone 74, and the pull wires 78, 86 including the pulley 80 are nested in the lower handle portion 14A. In this position, the hub 58 including the cap 62 capturing the intermediate sealable membrane 60 is supported therein by the fifth and sixth interior ribs 38 and 40 received in respective openings 38A, 40A with the distal hub end butting up against the fourth interior rib 36. A proximal portion 72A of the support shaft 72 rests on the second and third interior ribs 32, 34, received in respective openings 32A, 34A, with a proximal portion of the sleeve 68 being supported on the distal end wall 18A and the first interior rib 30 received in respective openings 20, 30A of the lower handle portion 14A.

The pulley 80 is received in a receptacle 92 upstanding from the sidewall 18 of the lower handle portion 14A between the second and third interior ribs 32, 34 with the wire guide retainer 82 nested in the carriage portion 64B of the lead screw assembly 64. However, the first hypo-tube 84 and the pull wire clamp block 88 secured to the second hypo-tube 89 are not in a nested relationship. Instead, they are only supported by their respective pull wires 78, 86 to which they are secured.

Next, the upper handle portion 14B is brought into engagement with the lower handle portion 14A. As previously discussed, the upper handle portion 14B is essentially a mirror image of the lower handle portion 14B including matching interior ribs 42, 44, 46, 48, 50 and 52 with respective openings 42A, 44A, 46A, 48A, 50A and 52A. The handle portions 14A, 14B are secured to each other with the screws 54 threaded into receptacles 56 in the lower handle portion 14A. As assembled, the lower and upper proximal end walls 18A, 24A, lower and upper distal end walls 18B, 24B and lower and upper interior rib pairs 30,42; 32,44; 34,46; 36,48; 38,50 and 40,52, meet each other with their respective openings being coincident.

In this position, there is unobstructed access through the proximal end walls 18B, 24B of the respective lower and upper handle portions 14A, 14B to the hub 58 funneling into the sheath lumen 16C. This construction also provides free and unobstructed access to the sealable membrane 60, which permits passage of instruments there through while substantially sealing about the periphery of the instrument and simultaneously preventing air embolism.

In use, a physician inserts the distal end 16A of the sheath 16 into the vasculature of a patient. As shown in FIGS. 2 and 13 to 15, the present bi-directional sheath assembly 10 provides for deflectable movement of the distal end 16A through a wide range both above and below a longitudinal axis defines by the longitudinal axis of the sheath 16. This deflectional motion is affected by rotational movement of the rotatable knob 66 in either a clockwise or counter clockwise direction.

Figure 13:
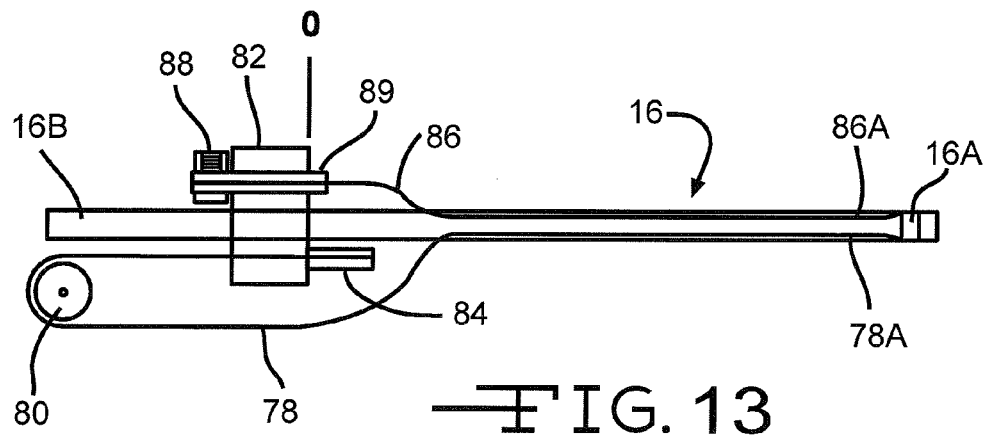
FIG. 13 is a schematic view showing the present bi-directional sheath 10 in a neutral position.

FIGS. 1 and 13 first show the deflectable distal end 16A of the sheath in a neutral or generally horizontal position, neither deflected upwardly or downwardly. In the schematic drawing shown of FIG. 13, it can be seen that the wire guide retainer 82 is in a neutral position designated by its forward or proximal side being aligned with the neutral mark "0". In this neutral position, the first hypo-tube 84 secured to the first pull wire 78 rests against the distal side of the wire guide retainer 82 and the wire clamp block 88 secured to the second hypo-tube 89 on the second pull wire 86 rests against the rearward or proximal side thereof.

Figure 14:
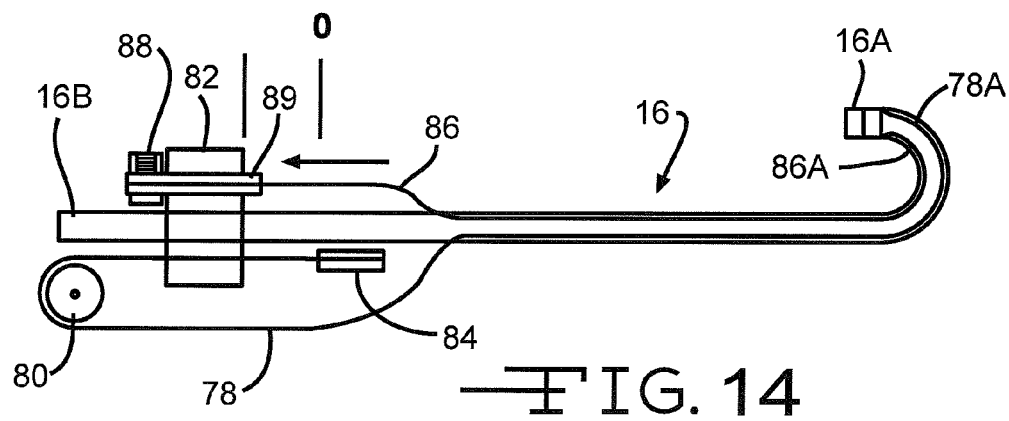
FIG. 14 is a schematic view showing the present bi-directional sheath 10 having its distal sheath end 16A deflected upwardly.

Then, if it is desired to deflect the distal sheath end 16A in an upwardly direction as shown by the dashed lines in FIG. 2 and in the schematic of FIG. 14, the knob 66 is rotated in a clockwise direction. This causes the sleeve 68 threadingly engaged with the threaded screw portion 64A to translate along the lead screw 64 in a backwards direction towards the proximal end of the handle 14. As the lead screw assembly 64 translates backwardly, the wire guide retainer 82 contacting the wire clamp block 88 secured to the second hypo-tube 89 on the second pull wire 86 moves in a rearwardly direction. This movement of the wire guide retainer 82 against the wire clamp block 88 causes the second pull wire 86 to move in a backwardly direction with respect to the sheath 16. As the wire clamp block 88 and the second pull wire 86 move backwardly (as shown by the forward side of the wire guide retainer 82 being spaced proximally from the neutral mark "0"), force is transferred to the distal end 86A of the pull wire (FIG. 3), thereby causing the distal end 16A of the sheath 16

(FIG. 2) to deflect upwardly. The first pull wire 78 does not move during this manipulation as it is stiff enough to permit the wire guide retainer 82 to slide along a bore in the retainer.

Rotation of the knob 66 in an opposite, counter clockwise direction releases pressure from the wire clamp block 88 as the wire guide retainer 82 begins to move in a distal direction. Once the wire guide retainer 82 is back in the neutral position (as shown by the forward side of the wire guide retainer 82 being aligned with the neutral mark "0" in FIG. 13 and having its respective sides contacting both the first hypo-tube 84 and the wire clamp block 88), the distal sheath end 16A relaxes into its neutral, longitudinal orientation (FIG. 2), nether deflecting upwardly or downwardly.

Figure 15:
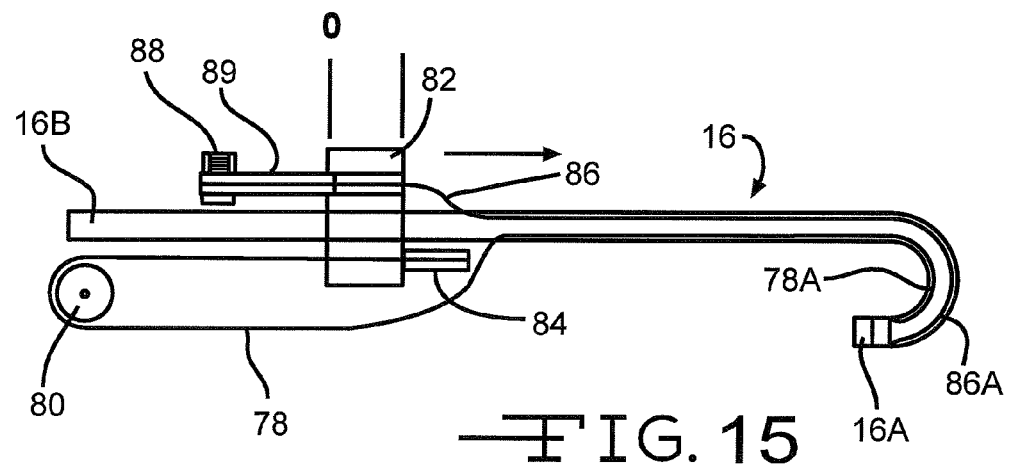
FIG. 15 is a schematic view showing the present bi-directional sheath 10 having its distal sheath end 16A deflected downwardly.

Should the physician want the distal sheath end 16A to deflect in a downwardly direction as shown by the solid lines in FIG. 2 and in the schematic of FIG. 15, the knob 66 is rotated in a counter clockwise direction. This causes the sleeve 68 threadingly engaged with the threaded screw portion 64A to translate along the lead screw 64 in a forward direction towards the distal end of the handle 14. As the lead screw assembly 64 translates forwardly, the wire guide retainer 82 moves the first hypo-tube 84 crimped onto the end of the first pull wire 78 in a forwardly direction. As the first hypo-tube 84 and the first pull wire 78 move forwardly, tension exerted on the pull wire 78 translates through the pulley 80 to the first end 78A of the pull wire, thereby causing the distal end 16A of the sheath 16 to deflect downwardly. As shown in FIG. 14, this results in wire guide retainer 82 being spaced from the wire clamp block 88 (the forward side of the wire guide retainer 82 is spaced distally from the neutral mark "0"). The second hypo-tube 89 and the second pull wire 86 do not move during this manipulation as they are stiff enough to permit sliding movement through the wire guide retainer 82.

Then, rotation of the knob 66 in an opposite, clockwise direction releases pressure from the first hypo-tube 84 so that the pull wire 78 rides in an opposite direction over the pulley 80. Once the wire guide retainer 82 is back into its neutral position contacting both the first hypo-tube 84 and the wire clamp block 88 (as shown by the forward side of the wire guide retainer 82 being aligned with the neutral mark "0" in FIG. 13), the distal sheath end 16A again relaxes into a neutral, longitudinal orientation, nether deflecting upwardly or downwardly.

It should be noted that the pull wires 78 and 86 are only secured to the deflectable sheath 16 at their respective distal ends 78A, 86A. The remainder of their lengths resides between the sheath body 16 and the previously described liner (not shown) forming the sheath lumen 16C. In any event, there is a "space" between the sheath 16 and the liner that permits movement of the pull wires there along.

Thus, it can be seen that the present invention provides a physician with a sheath assembly 10 that is capable of readily deflecting the distal sheath end 16A in any one of a myriad of direction, both upwardly and downwardly with respect to a longitudinal axis thereof. This provides the physician with a great degree of flexibility in maneuvering the distal end 16A of the sheath for performing a medical procedure inside the vasculature of a patient. Not only that, but the translational movement of the wire guide retainer 82 in a backward and forward direction to effect deflection movement of the sheath distal end 16A is built into a handle assembly 14 having a relatively compact size. This is a desirable attribute of the present bi-directional sheath as the handle fits nicely into the physician's palm to provide good tactile feel for sure and steady movement of the sheath distal end.

It is appreciated that various modifications to the inventive concepts described herein may be apparent to those of ordinary skill in the art without departing from the spirit and scope of the present invention as defined by the appended claims.

What is claimed is:

1. A deflectable sheath, which comprises:
    a) a tubular sheath providing a delivery lumen extending from a proximal sheath portion to a deflectable distal sheath end;
    b) a handle supporting the proximal sheath portion;
    c) a support shaft extending along a first longitudinal axis of a shaft bore from a distal shaft end to an open proximal shaft end, wherein the proximal sheath portion is received in the shaft bore with the delivery lumen of the sheath being in open communication to the proximal end of the handle;
    d) a threaded member housed inside the handle and longitudinally movable back and forth in a translational relationship along the support shaft, wherein the threaded member carries a wire guide retainer;
    e) a rotatable member supported on the support shaft in a rotatable, but non-translational relationship therewith and at a position distal to the wire guide retainer, wherein the rotatable member is threadingly engaged with the threaded member to effect selected translational movement of the threaded member carrying the wire guide retainer along the support shaft;
    f) wherein a first pull wire secured to the deflectable distal sheath end extends along the sheath and the support shaft before deviating at an acute angle past the wire guide retainer to a proximal change-of-direction device and then back at the acute angle to and then through the wire guide retainer to a proximal first pull wire end provided with a first stop member located distally of the wire guide retainer;
    g) wherein a second pull wire secured to the deflectable distal sheath end extends along the sheath and the support shaft to and through the wire guide retainer to a proximal second pull wire end provided with a second stop member located proximally of the wire guide retainer;
    h) wherein the rotatable member is manipulatable in a first direction to translate the threaded member carrying the wire guide retainer along the support shaft in a forwardly direction against the first stop member to apply a first pulling force on the first pull wire to thereby deflect the distal sheath end into a first orientation out of alignment with respect to a second longitudinal axis of the sheath; and
    i) wherein the rotatable member is manipulatable in a second direction, opposite the first direction, to translate the threaded member carrying the wire guide retainer along the support shaft in a rearwardly direction against the second stop member to apply a second pulling force on the second pull wire to thereby deflect the distal sheath end into a second orientation, out of alignment with respect to the second longitudinal axis of the sheath.

2. The deflectable sheath of claim 1 further including the support shaft being received on the sheath radially intermediate the threaded member and the proximal sheath portion.

3. The deflectable sheath of claim 1 wherein the wire guide retainer comprises a first bore slidingly receiving the first pull wire and a second bore slidingly receiving the second pull wire.

4. The deflectable sheath of claim 3 wherein the threaded member carrying the wire guide retainer is movable in the forwardly direction against the first stop member to apply the first pulling force on the first pull wire with the second pull wire and the second stop member slidable in the second bore in the wire guide retainer, and wherein the threaded member carrying the wire guide retainer is movable in the rearwardly direction against the second stop member to apply the second pulling force on the second pull wire with the first pull wire slidable in the first bore in the wire guide retainer.

5. The deflectable sheath of claim 1 wherein the threaded member includes a carriage portion that carries the wire guide retainer.

6. The deflectable sheath of claim 1 wherein the change of direction device is a pulley or a post.

7. The deflectable sheath of claim 1 wherein the first orientation of the deflected distal sheath end is substantially opposite the second orientation.

8. The deflectable sheath of claim 1 wherein, the first and second pull wires reside between the tubular sheath and a liner.

9. The deflectable sheath of claim 1 wherein the first and second pull wires are provided with respective anchors at the deflectable sheath end.

10. The deflectable sheath of claim 1 wherein the first and second pull wires reside on diametrically opposite sides of the tubular sheath.

11. The deflectable sheath of claim 1 wherein the first and second pull wires are in a slidable relationship with respective bores in the wire guide retainer.

12. The deflectable sheath of claim 1 wherein the rotatable member comprises a plurality of protrusions spaced about its periphery.

13. The deflectable sheath of claim 1 wherein the proximal portion of the sheath connects to a funnel-shaped hub.

14. The deflectable sheath of claim 13 wherein the hub supports a sealable membrane.

15. The deflectable sheath of claim 1 wherein the proximal portion of the sheath includes a side port.

16. The deflectable sheath of claim 1 wherein the support shaft provides opposed grooves extending parallel to the longitudinal axis of the shaft bore and the first and second pull wires reside in the respective grooves where they extend along the support shaft in a co-axial relationship with the shaft bore.

17. A deflectable sheath, which comprises:
a) a tubular sheath providing a delivery lumen, extending from a proximal sheath portion to a deflectable distal sheath end;
b) a handle supporting the proximal sheath portion;
c) a support shaft extending along a first longitudinal axis of a shaft bore from a distal shaft end to an open proximal shaft end, wherein the support shaft provides spaced apart first and second grooves extending parallel to the first longitudinal axis of the shaft bore and wherein the proximal sheath portion is received in the shaft bore with the delivery lumen of the sheath being in open communication to the proximal end of the handle;
d) a threaded member housed, inside the handle and longitudinally movable back and forth in a translational relationship along the support shaft, wherein the threaded member includes a carriage carrying a wire guide retainer;
e) a rotatable member supported on the support shaft in a rotatable, but non-translational relationship therewith and at a position distal to the wire guide retainer carried by the carriage, wherein the rotatable member is threadingly engaged with the threaded member to effect selected translational movement of the threaded member and the carriage carrying the wire guide retainer along the support shaft;
f) wherein a first pull wire secured to the deflectable distal sheath end extends along the sheath and the first groove of the support shaft before deviating at an acute angle past the wire guide retainer to a proximal pulley and then back at the acute angle to and then through a first bore in the wire guide retainer to a proximal first pull wire end provided with a first stop member located distally of the wire guide retainer;
g) wherein a second pull wire secured to the deflectable distal sheath end extends along the sheath and the second groove in the support shaft to and through a second bore in the wire guide retainer to a proximal second pull wire end provided with a second stop member located proximally of the wire guide retainer;
h) wherein the rotatable member is manipulatable in first direction to translate the threaded member and the carriage carrying the wire guide retainer along the support shaft in a forwardly direction against the first stop member to apply a first pulling force on the first pull wire to thereby deflect the distal sheath end into a first orientation out of alignment with respect to a second longitudinal axis of the sheath; and
i) wherein the rotatable member is manipulatable in a second direction, opposite the first direction, to translate the threaded member carrying the wire guide retainer along the support shaft in a rearwardly direction against the second stop member to apply a second pulling force on the second pull wire to thereby deflect the distal sheath end into a second orientation out of alignment with respect to the second longitudinal axis of the sheath.

18. The deflectable sheath of claim 17 wherein the threaded member carrying the wire guide retainer is movable in the forwardly direction against the first stop member to apply the first pulling force on the first pull wire with the second pull wire and the second stop member slidable in the second bore in the wire guide retainer, and wherein the threaded member carrying the wire guide retainer is movable in the rearwardly direction against the second stop member to apply the second pulling force on the second pull wire with the first pull wire slidable in the first bore in the wire guide retainer.

19. The deflectable sheath of claim 17 further including the support shaft being received on the sheath radially intermediate the threaded member and the proximal sheath portion.

20. The deflectable sheath of claim 17 wherein the wire guide retainer comprises a first bore slidingly receiving the first pull wire and a second bore slidingly receiving the second pull wire.

21. The deflectable sheath of claim 17 wherein the change of direction device is a pulley or a post.

22. The deflectable sheath of claim 17 wherein the first orientation of the deflected distal sheath end is substantially opposite the second orientation.

23. The deflectable sheath of claim 17 wherein the first and second pull wires reside between the tubular sheath and a liner.

24. The deflectable sheath of claim 17 wherein the first and second pull wires are provided with respective anchors at the deflectable sheath end.

25. The deflectable sheath of claim 17 wherein the first and second pull wires reside on diametrically opposite sides of the tubular sheath.

26. The deflectable sheath of claim 17 wherein the first and second pull wires are in a slidable relationship with respective bores in the wire guide retainer.

27. The deflectable sheath of claim 17 wherein the rotatable member comprises a plurality of protrusions spaced about its periphery.

28. The deflectable sheath of claim 17 wherein the proximal portion of the sheath connects to a funnel-shaped hub.

29. The deflectable sheath of claim 28 wherein the hub supports a sealable membrane.

30. The deflectable sheath of claim 17 wherein the proximal portion of the sheath includes a side port.

31. The deflectable sheath of claim 17 wherein the first and second pull wires reside in the respective first and second grooves where they extend along the support shaft in a co-axial relationship with the shaft bore.

32. A deflectable sheath, which comprises:
   a) a tubular sheath providing a delivery lumen extending from a proximal sheath portion to a deflectable distal sheath end;
   b) a handle supporting the proximal sheath portion;
   c) a support shaft extending along a first longitudinal axis of a shaft bore from a distal shaft end to an open proximal shaft end, wherein the support shaft provides opposed first and second grooves extending parallel to the first longitudinal axis of the shaft bore and wherein the proximal sheath portion is received in the shaft bore with the delivery lumen of the sheath being in open communication to the proximal end of the handle;
   d) a threaded member housed inside the handle and longitudinally movable back and forth in a translational relationship along the support shaft, wherein the threaded member includes a wire guide retainer;
   e) a rotatable member supported on the support shaft in a rotatable, but non-translational relationship therewith and at a position distal to the wire guide retainer, wherein the rotatable member is threadingly engaged with the threaded member to effect selected translational movement of the threaded member carrying the wire guide retainer along the support shaft;
   f) wherein a first pull wire secured to the deflectable distal sheath end extends along the sheath and the first groove of the support shaft in a co-axial relationship with the shaft bore before deviating at an acute angle past the wire guide retainer to a proximal pulley and then back at the acute angle to and then through a first bore in the wire guide retainer to a proximal first pull wire end provided with a first stop member located distally of the wire guide retainer;
   g) wherein a second pull wire secured to the deflectable distal sheath end extends along the sheath and the second groove in the support shaft in a co-axial relationship with the shaft bore to and through a second bore in the wire guide retainer to a proximal second pull wire end provided with a second stop member located proximally of the wire guide retainer;
   h) wherein the rotatable member is manipulatable in a first direction to translate the threaded member and the carriage carrying the wire guide retainer along the support shaft in a forwardly direction against the first stop member to apply a first pulling force on the first pull wire to thereby deflect the distal sheath end into a first orientation out of alignment with respect to a second longitudinal axis of the sheath; and
   i) wherein the rotatable member is manipulatable in a second direction, opposite the first direction, to translate the threaded member carrying the wire guide retainer along the support shaft in a rearwardly direction against the second stop member to apply a second pulling force on the second pull wire to thereby deflect the distal sheath end into a second orientation out of alignment with respect to the second longitudinal axis of the sheath.

* * * * *